United States Patent [19]

Takamizawa et al.

[11] Patent Number: 4,593,112
[45] Date of Patent: Jun. 3, 1986

[54] METHOD FOR THE PREPARATION OF A TERT-HYDROCARBYL SILYL COMPOUND

[75] Inventors: Minoru Takamizawa; Toshinobu Ishihara; Akira Yamamoto, all of Niigata, Japan

[73] Assignee: Shin-Etsu Chemical Co., Ltd., Tokyo, Japan

[21] Appl. No.: 723,669

[22] Filed: Apr. 16, 1985

[30] Foreign Application Priority Data

Apr. 17, 1984 [JP] Japan .................................. 59-77156

[51] Int. Cl.[4] ............................................... C07F 7/08
[52] U.S. Cl. .................................................... 556/480
[58] Field of Search ......................................... 556/480

[56] References Cited

U.S. PATENT DOCUMENTS

| | | | |
|---|---|---|---|
| 2,413,049 | 12/1946 | Hyde | 556/480 |
| 2,426,122 | 8/1947 | Rust et al. | 556/480 |
| 2,759,959 | 8/1956 | Frisch | 556/480 |
| 2,872,471 | 2/1959 | Ramsden et al. | 556/480 |
| 2,894,012 | 7/1959 | Ramsden et al. | 556/480 |
| 3,426,087 | 2/1969 | Ashby | 556/480 X |

Primary Examiner—Paul F. Shaver
Attorney, Agent, or Firm—Toren, McGeady, Stanger, Goldberg & Kiel

[57] ABSTRACT

A tert-hydrocarbyl, e.g. tert-butyl, silyl compound can be synthesized easily according to the method of the invention in which a tert-hydrocarbylmagnesium halide as a Grignard reagent is reacted with a silane compound having at least one silicon-bonded hydrogen atom and at least one silicon-bonded halogen atom simultaneously in a molecule in a suitable organic solvent so that the halogen atom in the latter reactant is replaced with the tert-hydrocarbyl group in the former reactant to give the desired tert-hydrocarbyl silyl compound in a high yield without the safety problem in the conventional method using a tert-alkyl lithium as the reactant.

3 Claims, No Drawings

METHOD FOR THE PREPARATION OF A TERT-HYDROCARBYL SILYL COMPOUND

BACKGROUND OF THE INVENTION

The present invention relates to a method for the preparation of a tert-hydrocarbyl silyl or a tert-alkyl silyl compound or, more particularly, to a method for introducing a tert-hydrocarbyl group directly bonded to a silicon atom in an organosilicon compound.

As a method for introducing a silicon-bonded tert-hydrocarbyl group into an organosilicon compound, a method is known in the prior art in which a tert-alkyl lithium is used (see, for example, *Journal of Organic Chemistry*, volume 43, page 3649, 1978 and Journal of the American Chemical Society, volume 76, page 1030, 1954). This method, however, is practically not applicable to the industrial production of such an organosilicon compound due to several disadvantages and problems that the tert-alkyl lithium is prepared in a process in which metallic lithium having a very high melting point of 190° C. must be finely divided in a molten state into a fine particulate form having a particle diameter of a few μm using a special apparatus while utmost care is essential in order to avoid any danger caused by the highly active metallic lithium and tert-alkyl lithiums may spontaneously catch fire when contacted with the atmospheric air so that handling of a large amount thereof is always accompanied by a great danger.

A general method for introducing a hydrocarbyl group into a silicon compound is the utilization of a Grignard reagent but this method is not applicable when the silicon compound to be reacted with the Grignard reagent is silicon tetrachloride, ethyl orthosilicate or an organosilane compound such as trimethyl chlorosilane so that no tert-hydrocarbyl-substituted silyl compound can be obtained from these silicon compounds (see, for example, Journal of the *American Chemical Society*, volume 70, page 2876, 1948).

SUMMARY OF THE INVENTION

An object of the present invention is therefore to provide an industrially advantageous method for the preparation of a tert-hydrocarbyl silyl compound or for introducing a silicon-bonded tert-hydrocarbyl group into a silicon compound.

Thus, the method of the present invention completed with the above described object comprises reacting a Grignard reagent represented by the general formula $R^1MgX$, in which $R^1$ is a tert-hydrocarbyl or, in particular, tert-alkyl group and X is a halogen atom, and a silane compound represented by the general formula $X_mR^2_nSiH_{4-m-n}$, in which $R^2$ is a monovalent hydrocarbon group, X is a halogen atom, m is 1, 2 or 3 and n is zero, 1 or 2 with the proviso that m+n does not exceed 3, in an organic solvent.

DETAILED DESCRIPTION OF THE PREFERRED EMBODIMENTS

The above described method of the present invention has been completed on the basis of a new discovery that the desired reaction of introducing a tert-hydrocarbyl group into a silicon compound by use of a Grignard reagent can proceed satisfactorily only when a Grignard reagent having a tert-hydrocarbyl or tert-alkyl group is reacted with a silicon compound having at least one silicon-bonded hydrogen atom and at least one silicon-bonded halogen atom simultaneously in a molecule so that the tert-hydrocarbyl group of the Grignard reagent is readily substituted for the halogen atom in the silicon compound to give the desired tert-hydrocarbyl silyl compound. The present invention is also a result of the extensive studies for the types of the Grignard reagent and the silicon compound as well as the conditions for the reaction including various parameters such as the kind of the organic solvent as the reaction medium, reaction temperature, etc.

The Grignard reagent used in the method of the present invention is represented by the general formula $R^1MgX$, in which $R^1$ is a tert-alkyl or tert-aralkyl group such as tert-butyl, 1,1-dimethylpropyl, 1,1-diethylpropyl, 1,1-dimethylbenzyl and the like groups and X is a halogen atom which may be a chlorine atom or a bromine atom. Particular examples of the Grignard reagent include tert-butylmagnesium chloride, 1,1-dimethylpropylmagnesium chloride, 1,1-diethylpropylmagnesium chloride, 1,1-dimethylbenzylmagnesium chloride and the like.

The silicon compound to be reacted with the above described Grignard reagent is a silane compound represented by the general formula $X_mR^2_nSiH_{4-m-n}$, in which $R^2$ is a monovalent hydrocarbon group selected from the class consisting of alkyl groups such as methyl, ethyl and propyl groups, alkenyl groups such as vinyl and allyl groups and aryl groups such as phenyl group as well as those substituted groups obtained by the replacement of all or a part of the hydrogen atoms in the above named hydrocarbon groups with substituents such as halogen atoms and the like and X is a halogen atom which may be a chlorine atom or a bromine atom. The suffixes m and n are each an integer of 1, 2 or 3 and zero, 1 or 2, respectively, with the proviso that m+n does not exceed 3. Particular examples of the silicon compound included trichlorosilane, methyl dischlorosilane, ethyl dichlorosilane, phenyl dichlorosilane, chloromethyl dichlorosilane and the like.

The step preceding the method of the present invention is the preparation of the Grignard reagent which can readily be obtained by the reaction of metallic magnesium and a tert-hydrocarbyl halide of the formula $R^1X$, in which $R^1$ and X each have the same meaning as defined above, in a suitable organic solvent. The reaction of the thus prepared Grignard reagent with the silicon compound proceeds according to the following reaction equation:

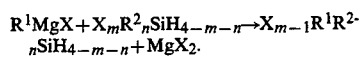

This reaction is performed in an inert organic solvent as the reaction medium and a solvent suitable for the purpose is exemplified by ether solvents such as diethyl ether, tetrahydrofuran and the like, phosphoramide solvents such as hexamethylphosphoryl triamide and aromatic hydrocarbon solvents such as benzene and toluene. It is optional to use these solvents as a mixture of two kinds or more according to need.

The reaction of the inventive method is performed at a temperature in the range from 10° to 150° C. or, preferably, from 40° to 100° C. in an atmosphere of an inert gas such as nitrogen and arogen because even a trace amount of oxygen in the atmosphere may react with the Grignard reagent to cause a decrease in the yield of the desired reaction product.

The method of the present invention provides a possibility of advantageously obtaining the desired tert-hydrocarbyl silyl compound in a high yield without any problem of safety even by using no special apparatus. In addition to the good convertibility into a tert-hydrocarbyl dialkyl halosilane and other organosilicon compounds useful as an intermediate of various organosilicon products, the tert-hydrocarbyl silyl compound obtained by the inventive method has an applicability as a special silylating agent useful in the synthesis of steroids, prostaglandins and other physiologically active compounds by virtue of the high steric selectivity and higher chemical stability than those of the trimethylsilyl ether type due to the presence of a bulky tert-hydrocarbyl group.

In the following, the method of the present invention is described in more detail by way of examples followed by a description of an application of the compound obtained by the inventive method.

EXAMPLE 1

Into a flask of 500 ml capacity were introduced 12 g (0.5 mole) of metallic magnesium, 300 ml of tetrahydrofuran and a bit of iodine and then 46.3 g (0.5 mole) of tert-butyl chloride were added dropwise into the reaction mixture in the flask kept at a temperature of 40° to 50° C. under a stream of nitrogen gas over a period of 1 hour followed by further continued agitation of the mixture at 55° C. for additional 1 hour to give tert-butylmagnesium chloride as the Grignard reagent.

Thereafter, 57.5 g (0.5 mole) of methyl dichlorosilane were added dropwise into the Grignard mixture in the flask kept at a temperature of 66° C. over a period of 1 hour followed by further continued agitation of the mixture at the same temperature for additional 3 hours to complete the reaction. During this period, a white crystalline material precipitated in the mixture. The reaction mixture after completion of the reaction was filtrated with suction and the filtrate was subjected to distillation. The fraction collected in the temperature range from 85° to 95° C. contained 47.8 g of tert-butyl methyl chlorosilane corresponding to a yield of 70% based on the calculated amount of the product.

EXAMPLE 2

Into a flasx of 500 ml capacity were introduced 12 g (0.5 mole) of metallic magnesium, 100 ml of tetrahydrofuran, 250 ml of toluene and a bit of iodine and then 53.3 g (0.5 mole) of 1,1-dimethylpropyl chloride were added dropwise into the reaction mixture in the flask kept at a temperature of 40° to 50° C. under a stream of nitrogen gas over a period of 1 hour followed by further continued agitation of the mixture at 60° C. for additional 1 hour to give 1,1-dimethylpropylmagnesium chloride as the Grignard reagent.

Thereafter, 47.3 g (0.5 mole) of dimethyl chlorosilane were added dropwise into the Grignard mixture in the flask kept at a temperature of 80° C. over a period of 1 hour followed by further continued agitation of the mixture kept at 90° C. for additional 4 hours. After cooling, the reaction mixture was poured into 300 ml of water and the organic solution taken by phase separation was distilled to give 23.4 g of 1,1-dimethylpropyl dimethyl silane corresponding to a yield of 36% based on the calculated amount.

APPLICATION EXAMPLE

Into a flask of 500 ml capacity were introduced 12 g (0.5 mole) of metallic magnesium, 150 ml of tetrahydrofuran and a bit of iodine and then 30.3 g (0.6 mole) of methyl chloride were blown into the reaction mixture in the flask kept at a temperature of 40° to 50° C. under an atmosphere of nitrogen gas over a period of 2 hours followed by further continued agitation of the mixture kept at 55° C. for additional 1 hour to give methylmagnesium chloride as the Grignard reagent.

Thereafter, 47.8 g of tert-butyl methyl chlorosilane prepared in Example 1 were added dropwise into the Grignard mixture in the flask kept at a temperature of 20° to 30° C. followed by further continued agitation of the mixture at 40° C. for additional 1 hour to complete the reaction. Then, the reaction mixture was cooled and poured into 300 ml of water and the organic solution taken by phase separation was distilled to give 40 g of tert-butyl dimethyl silane in a yield of 98.5% based on the calculated amount.

In the next place, 40 g of the thus prepared tert-butyl dimethyl silane and 100 g of carbon tetrachloride were introduced into a flask of 300 ml capacity and then 25.7 g of chlorine gas were introduced into the reaction mixture in the flask kept at a temperature of 20° to 30° C. over a period of 3 hours. Then, nitrogen gas bubbled into the reaction mixture for 2 hours to expel the chlorine and hydrogen chloride dissolved in the mixture followed by distillation thereof. The fraction collected in the temperature range of 128° to 138° C. in this distillation contained 44.1 g of tert-butyl dimethyl chlorosilane corresponding to a yield of 85% based on the calculated value. This silane compound is known to be useful as a special silylating agent.

We claim:

1. A method for the preparation of a tert-hydrocarbyl silyl compound having at least one hydrogen atom directly bonded to the silicon atom which comprises reacting a Grignard reagent represented by the general formula $R^1MgX$, in which $R^1$ is a tert-hydrocarbyl group and X is a halogen atom, and a silane compound represented by the general formula $X_mR^2_nSiH_{4-m-n}$, in which $R^2$ is a monovalent hydrocarbon group, X is a halogen atom, m is 1, 2 or 3 and n is zero, 1 or 2 with the proviso that m+n does not exceed 3, in an organic solvent.

2. The method as claimed in claim 1 wherein the reaction of the Grignard reagent and the silane compound is performed at a temperature in the range from 10° to 150° C.

3. The method as claimed in claim 1 wherein the organic solvent is selected from the class consisting of ether solvents, phosphoramide solvents and aromatic hydrocarbon solvents.

* * * * *